(12) United States Patent
Nishino

(10) Patent No.: US 6,437,355 B1
(45) Date of Patent: Aug. 20, 2002

(54) APPARATUS FOR JUDGING WHETHER BUMP HEIGHT IS PROPER OR NOT

(75) Inventor: Akira Nishino, Ogaki (JP)

(73) Assignee: Ibiden Co., Ltd., Ogaki (JP)

( * ) Notice: Subject to any disclaimer, the term of this patent is extended or adjusted under 35 U.S.C. 154(b) by 0 days.

(21) Appl. No.: 09/508,698

(22) PCT Filed: Sep. 29, 1998

(86) PCT No.: PCT/JP98/04358

§ 371 (c)(1),
(2), (4) Date: Mar. 30, 2000

(87) PCT Pub. No.: WO99/17074

PCT Pub. Date: Apr. 8, 1999

(30) Foreign Application Priority Data

Sep. 30, 1997 (JP) .............................................. 9-266580

(51) Int. Cl.[7] .............................................. G01B 11/00
(52) U.S. Cl. ............................ 250/559.19; 250/559.08; 250/559.2; 250/559.34; 356/625
(58) Field of Search ....................... 250/559.07, 559.08, 250/559.19, 559.2, 559.22, 559.23, 559.34, 222.1; 356/601, 606, 625, 237.4, 237.5; 257/737, 738, 780; 228/8, 9, 104

(56) References Cited

U.S. PATENT DOCUMENTS 5,906,309 A * 5/1999 Hashimoto et al. .... 250/559.23
5,986,763 A * 11/1999 Inoue ......................... 356/625

FOREIGN PATENT DOCUMENTS

| JP | 4-231852 | 8/1992 |
| JP | 8-122273 | 5/1996 |
| JP | 8-193807 | 7/1996 |
| JP | 9-159415 | 6/1997 |

* cited by examiner

*Primary Examiner*—Kevin Pyo
(74) *Attorney, Agent, or Firm*—Oblon, Spivak, McClelland, Maier & Neustadt, P.C.

(57) ABSTRACT

An apparatus to check a height of a bump includes a measuring device and a determining device. The measuring device is configured to measure a distance between an image position in an image of a reference object reflected in a surface of the bump and a predetermined position which is positioned on a line connecting the image position and a center of the bump such that the image position exists between the center and the predetermined position. The determining device is configured to determine whether the height of the bump is within a predetermined range by comparing the distance with a reference distance.

9 Claims, 14 Drawing Sheets

APPARATUS FOR JUDGING WHETHER BUMP HEIGHT IS PROPER OR NOT

TECHNICAL FIELD

The present invention relates to an apparatus for judging a bump, which is established on printed circuit boards, etc., whether the bump height is proper or not.

BACKGROUND ART

Heretofore, on a printed circuit board and on a semiconductor chip, a bump is formed as an electrical connecting means with other electronic component. It is necessary that a height of the bump be in a predetermined range. For example, when a height of a solder bump formed on a printed circuit board is too low, because an amount of solder, which forms the bump, is too small, electric connection becomes inadequate. On the contrary, when the height of the bump is too high, because the amount of the solder, which forms the bump, is too large, it short-circuits with adjacent bumps when the printed circuit board is connected to electronic circuit elements such as IC or the like.

Moreover, further efficiency improvement is necessary for the judging whether bumps are proper or not, as the number of the bumps exceeds 1000 on a recent large-scale integrated circuit (LSI).

The present invention has been made in order to cope with the above-described demand. An object of the present invention is to provide an apparatus for judging a bump height, capable of efficiently and moreover reliably judging whether a bump height is proper or not.

DISCLOSURE OF THE INVENTION

To achieve the object, the first invention is an apparatus for judging whether a bump height is proper or not includes: an imaging means disposed above a bump as an object to be measured, and configured to capture a surface image of a surface of the bump; a reference object disposed so that an image of the reference object viewed from the imaging means is reflected on the surface of the bump; a judgment means configured to measure, based on image data obtained by the imaging means, a distance between an image position of the image on the surface of the bump and a predetermined position, which is on an edge side of a radial direction of the bump when viewed from the image position, and to judge whether the bump height is proper or not by comparing a value of the distance with a preset reference value.

The second invention is an apparatus for judging whether a bump height is proper or not in the first invention, wherein the predetermined position is an edge position of the bump.

The third invention is an apparatus for judging whether a bump height is proper or not in the first invention, wherein the predetermined position is a position on the surface of the bump of a second reference object, which is disposed so that an image of the second reference object viewed from the imaging means, is reflected on the surface of the bump.

The forth invention is an apparatus for judging whether a bump height is proper or not in the first invention, wherein the position of the image on the surface of the bump is a position in the bump top side of the image and the predetermined position is a position in the bump edge side of the image.

(OPERATION)

In the first invention, the imaging means is disposed above the bump in order to settle multiple bumps in one imaging field. And, the image data of the bump surface obtained by the imaging means contain data, which can calculate a value of a distance between 2 points being located in a bump radial direction. Moreover, the value of the distance has a correlation for the bump height. Therefore, the time for the judging where the bump height is proper or not can be shortened, though the first invention is a simple apparatus.

Especially, it becomes that in case of a bump with a shape in which a height as an edge portion increases rapidly (so usual bump does), the position in the bump edge side of superscription of two points is hard to receive an effect of the bump height in comparison with the position in the bump top side, and becomes constant. Therefore, if position data of the bump edge side are handled as a constant value, the apparatus of this first invention can also reduce image processing data volume. So high speed judging is more possible for this apparatus.

In the second invention, as the position of the bump edge side is fixed in the bump edge, the position data become constant. So this apparatus can realize the high-speed judging with accuracy.

In the third invention, the position of the bump edge side can be set at the position of the desire. Therefore, even if there is a point of an improper surface state in the bump, the measuring point can be set by the avoiding point. So high-precise and stabilized judging is possible for this apparatus.

The forth invention is an apparatus for judging whether a bump height is proper or not of a simple composition which can achieve the action of the third invention in reference object of one.

BEST MODES OF CARRYING OUT THE INVENTION (First Embodiment)

Figure 1:
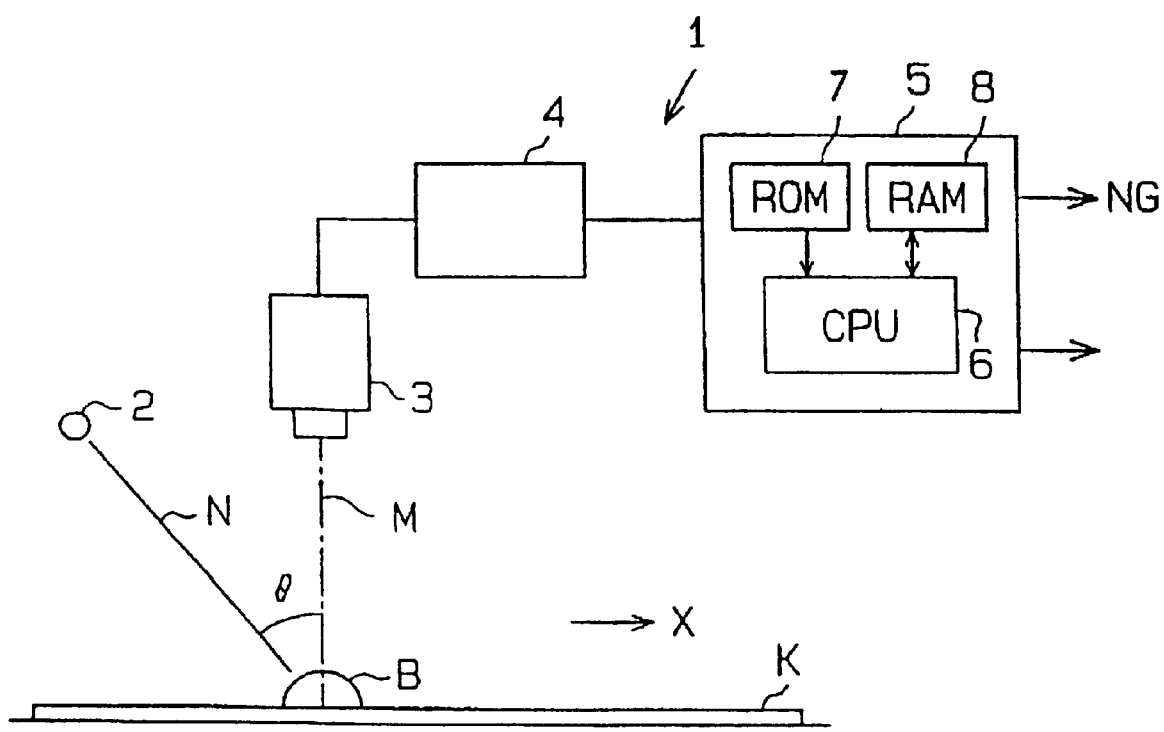
FIG. 1 is a schematic drawing of an apparatus for judging whether a bump height is proper or not according to an embodiment of the first invention.

First embodiment, which materialized the second invention, is explained with reference to FIGS. 1–7. FIG. 1 shows a whole summary configuration of this embodiment of an apparatus 1 for judging whether a bump height is proper or not. In this figure, the apparatus 1 for judging whether a bump height is proper or not includes a light emission apparatus 2 as a point light source, which is a reference object; an imaging device 3, which is an imaging means; an image processing device 4, which is a judgment means; and a computer 5.

The imaging device 3 is composed of an area sensor type CCD camera. The imaging device 3 is connected with the computer 5 through the image processing device 4. In this embodiment, the imaging device 3 is disposed right above a bump B, which is an object to be measured established on a printed circuit board K.

Figure 5:
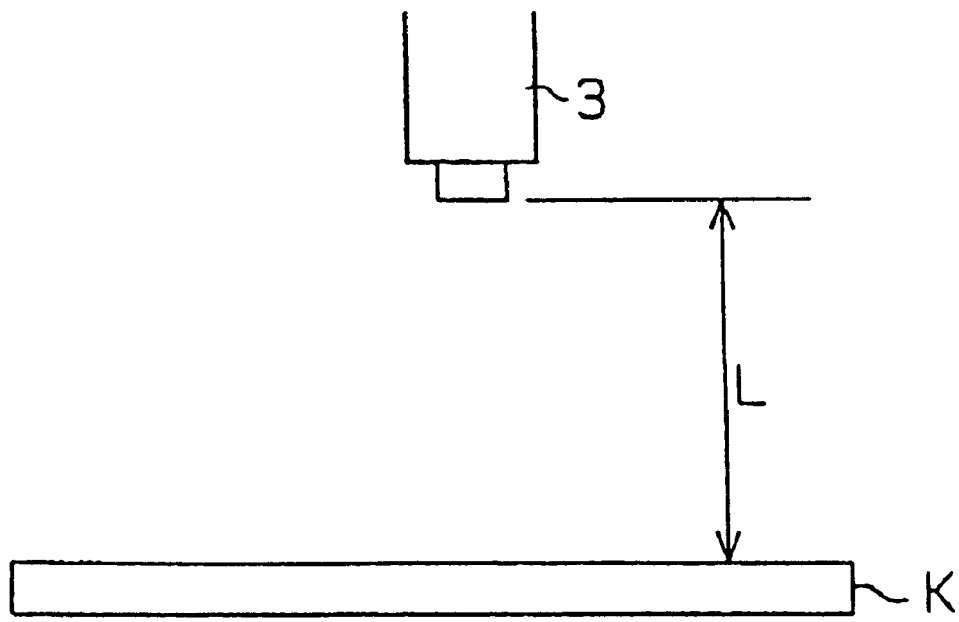
FIG. 5 is an explanatory drawing, which shows a clearance between the printed circuit board and a CCD camera in the same embodiment.

And, as shown in FIG. 5, in this embodiment, a distance L between the printed circuit board K and a lens provided in the CCD camera as the imaging device 3 is 300 mm. And, the lens diameter is 50 mm, and a picture element number (m×n) of the CCD is 480×640 (a range of capturing an image at one time is 10 mm×10 mm).

And, the light emission apparatus 2 consists of a single unit of an LED, which is separate from the bump B by 600 mm, and emits light by a not illustrating driving circuit. In this embodiment, the light emission equipment 2 is placed in the oblique upper part of the bump B, which is provided on the printed circuit board K. When viewed from a center of the bump B, this light emission apparatus 2 is located at an angle $\theta$ of 45 degrees from a vertical line M (an imaging central axis of the imaging device 3), which passes a top of the bump B and extends from the center of the bump B. It is desirable that this angle $\theta$ is determined such that a shadow of an adjoining bump B does not affect imaging.

Figure 6:
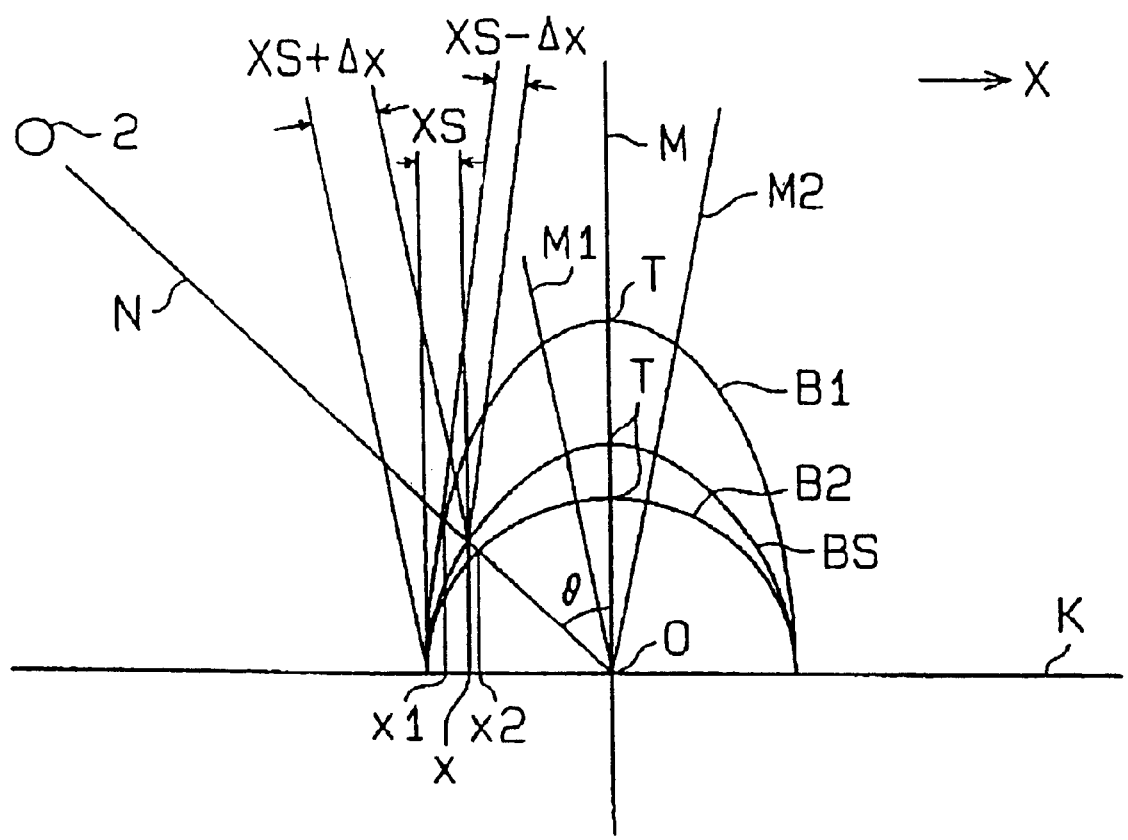
FIG. 6 is an explanatory drawing of a situation in which the image of the light source is reflected on the bump of which the height differs in the same embodiment.

FIG. 6 shows a relationship between the bump B, the light emission apparatus (LED) 2, and the imaging central axis M. The position which the imaging central axis M passes, on the printed circuit board K is supposed to be a cardinal point O (it is called a center point of the bump B). An optic axis from the light emission apparatus (LED) 2, which passes the cardinal point O, is called an optic axis N. The angle $\theta$ which is formed between the imaging central axis M and the optic axis N is 45 degrees. Still, in FIG. 1 and in FIG. 6, on convenience of the description, the bump B is illustrated by enlarging.

The computer 5 has a central processing unit (CPU) 6, a read only memory (ROM) 7 which beforehand memorized control programs, etc., and a random access memory (RAM) 8 for temporarily memorizing operation results and for memorizing data necessary for an arithmetic processing, etc.

The CPU 6 of the computer 5 constitutes a length calculation means and a judgment means. The ROM 7 and the RAM 8 constitute a memory means. And, the light emission apparatus 2 constitutes an object to be measured and a light emission means. The imaging device 3 constitutes an imaging means.

Then, an operation of the apparatus 1 as described above for judging whether a bump height is proper or not will be explained. In FIG. 1, the printed circuit board K on which the bump B of predetermined number n is provided is set so that the bump B is located under the imaging devices 3. After the set completion, the light emission apparatus 2 emits light. Then, the image of the bump B is captured by the imaging device 3. With respect to the imaging data which is obtained by the imaging device 3, after various filter processing of noise rejection and of concentration normalization, etc. and binary coded processing are carried out in the image processing device 4, the imaging data are input into the computer 5.

The binary coded processing is carried out based on a predetermined binary threshold. That is to say, in the bump B surface, by the light emission of the light emission apparatus 2, the brightness of an image of a reflection region of the light emission apparatus 2 is high, and the brightness of an image of the other region is low. And the brightness of an image of the printed circuit board K on which the bump B is established is high. Then, the above-mentioned binary threshold is set so as to divide a part, which consists of the reflection region in the bump B of the light emission apparatus 2 and a region of the printed circuit board K, and a part, which consists of a main body part of the bump B. Data obtained by the above-mentioned various filter processing is called the following, image data.

Figure 7:
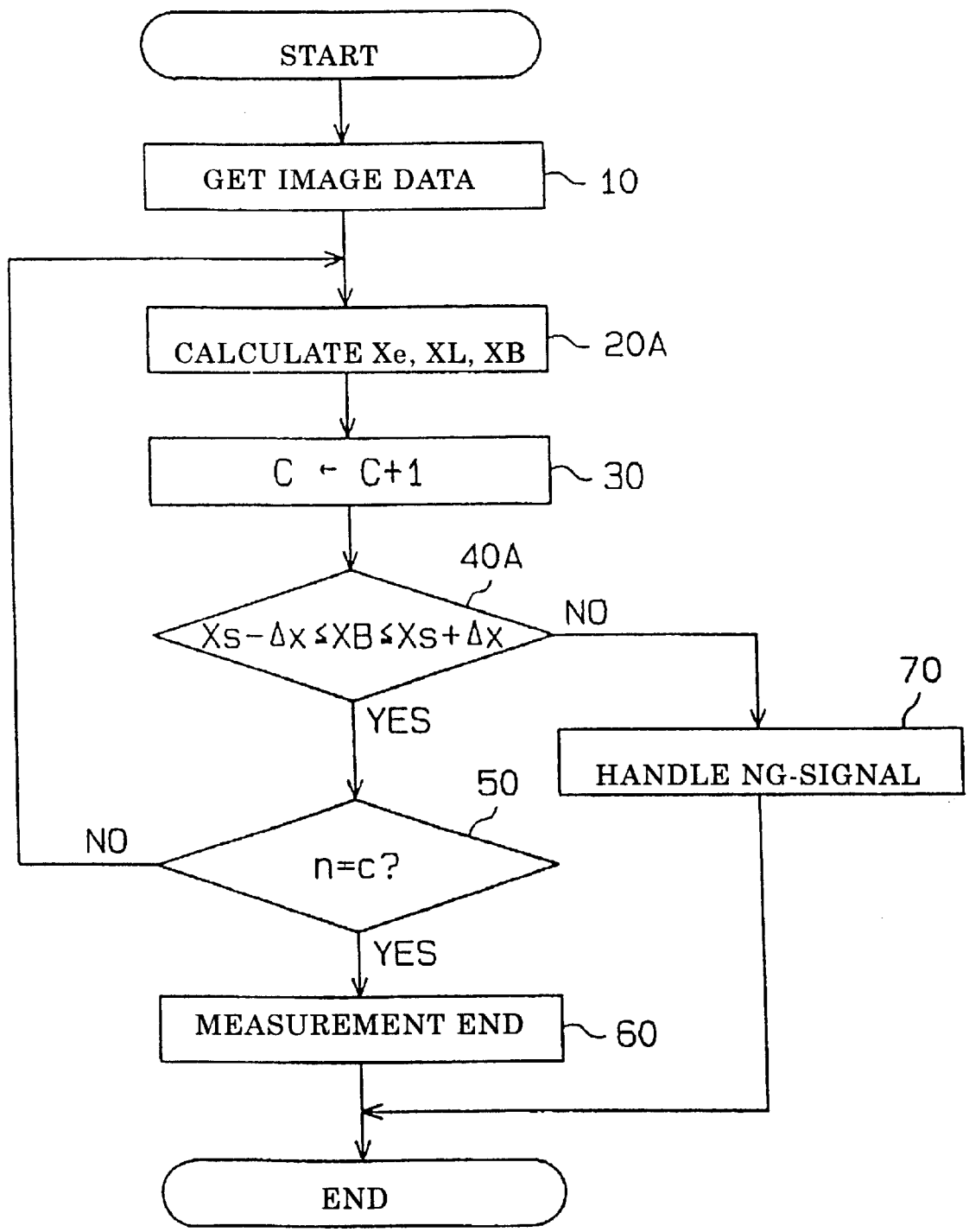
FIG. 7 is a flowchart of judging of the apparatus for judging whether a bump height is proper or not in the same embodiment.

Next, the CPU 6 of the computer 5 executes a bump height judging processing routine shown in FIG. 7. To begin with, in step 10, image data obtained by capturing an image at one time are read. At this step 10, based on the image data obtained by capturing an image at one time, the number n of bumps B in the imaging area is counted and the number n is stored in the RAM 8.

Next, the routine goes to step 20. In step 20, along an inspection line $\alpha$, the position of a bump edge e or the like is obtained and Xe, XL, XB are calculated.

It explains in detail the following. In this embodiment, an inspection direction of image data is set so as to be in parallel with the radial direction of the bump B. Within image data composed of picture elements of m×n pieces, picture elements along the inspection line $\alpha$ in a direction (an X direction) on the diameter of the bump B are chosen as an inspection region. The measurement operation is carried out along the X arrow direction from the side in the inspection region. Still, in FIG. 2, image data, which concern one bump B, are shown.

This measurement operation is carried out like the following. To begin with, on the inspection line $\alpha$, on the diameter of this bump B, the distance Xe between an origin O1 (a start point of the inspection line of the image data) and the bump edge e of this bump B is calculated and the distance XL between the origin O1 and the edge in a reflection region 2a of the light emission apparatus 2 on this bump B is calculated. Then, the XB, which is a difference in the Xe and the XL, is calculated.

In this embodiment, the bump edge e of the bump B corresponds to the second measuring point, the edge of the reflection region 2a of light emission apparatus 2 on the bump B corresponds to the first measuring point, and the XB corresponds to the distance between measuring points. In next step 30, one increment of a bump number counter C is done, and the routine shifts to step 40.

Then, in step 40, it is determined whether the distance XB between the measuring points calculated in aforesaid step 20 satisfies a reference value. And the reference value is beforehand memorized in the ROM7.

Aforesaid reference value is determined based on a distance XS between a bump edge e (a second measuring point)

and an edge (a first measuring point) of a reflection region 2a of the light emission apparatus 2 in picturizing an image of a bump BS (of the following, standard bump) of a proper height H under the aforesaid condition.

Still, the distance (see FIG. 2) between the first measuring point and the second measuring point has a correlation with the height H of the bump B. When a bump B2 is lower than the standard bump BS (see FIG. 6), an edge of a reflection region 2a of the light emission apparatus 2 which is reflected on the bump takes a position x2 which is shifted to the top T (center point O) of the bump. When a bump B1 is higher than the standard bump BS (see FIG. 6), an edge of a reflection region 2b of the light emission apparatus 2 which is reflected on the bump takes a position x1 which is shifted to the bump edge e.

Figure 2:
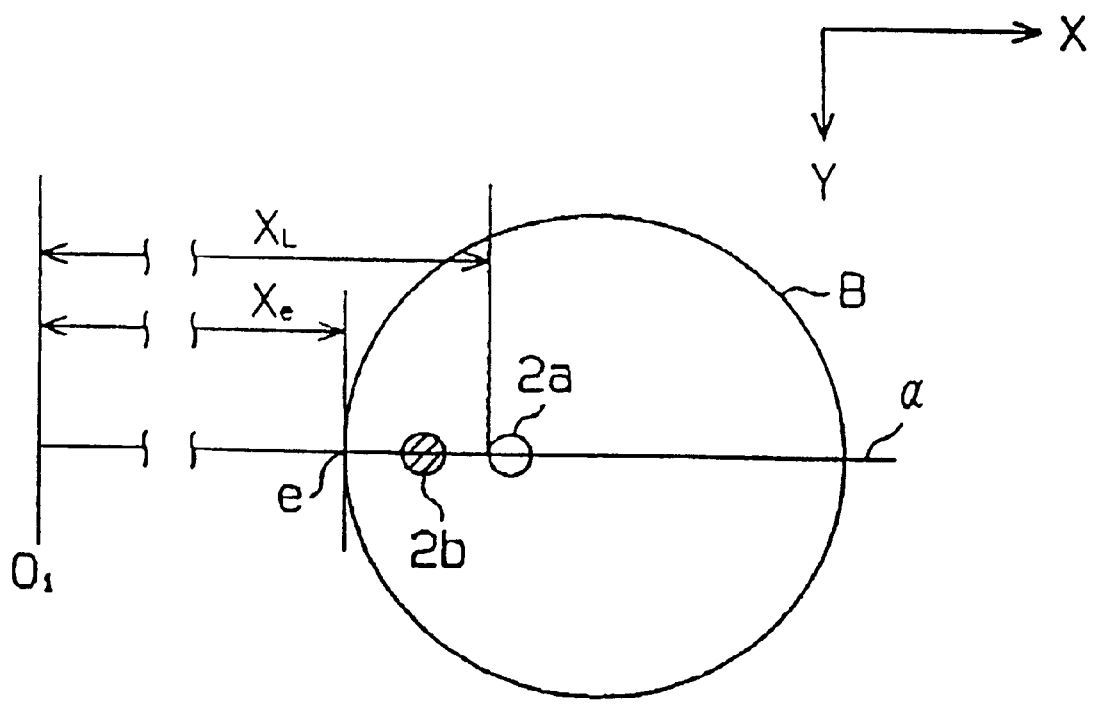
FIG. 2 is a plan of the bump including an image of a light source, which is reflected in the bump surface in the same embodiment.

For example, in FIG. 2, the reflection region 2b of the bump shown in the hatching shows a case in which it shifts more to the bump edge e side rather than the reflection region 2a. That is to say, it is proven that the bump related to the reflection region 2b, is higher than the bump related to the reflection region 2a.

Still, the bump B2, which is lower than the standard bump BS, is a case in which amounts of the bump formation material such as solder is less than that of the standard bump BS. Reversibly, the bump, which is higher than the standard bump BS, is a case in which amounts of the bump formation material such as solder is more than that of the standard bump BS.

Superscription reference value is explained here. The reference value is calculated by adding a detection error $\Delta x$ to the distance XS between the bump edge e (the second measuring point) which concerns the standard bump BS with aforesaid bump height H and the edge (the first measuring point) of the reflection region 2a of the light emission apparatus 2. Still, it is based that the detection error comes out on the reason of the following.

Figure 3:
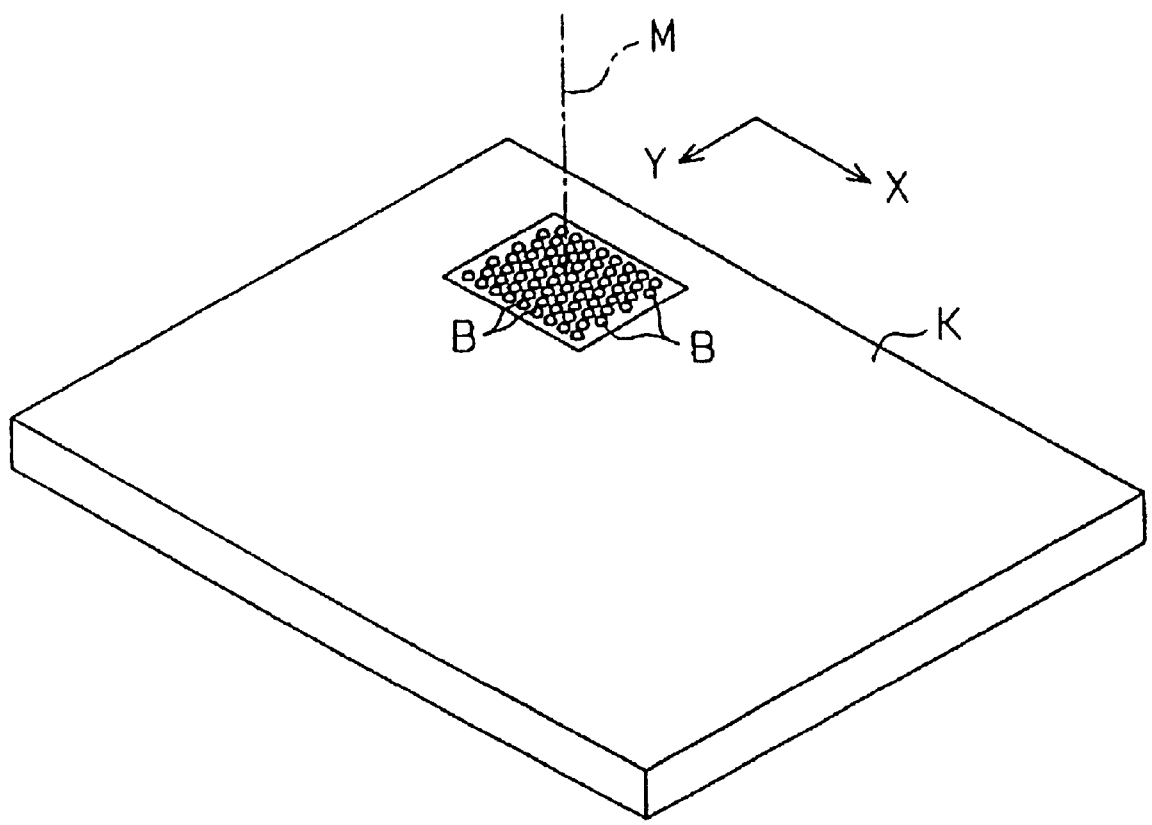
FIG. 3 is a strabismus figure, which shows an arrangement of solder bumps placed on a printed circuit board in the same embodiment.

Though in FIG. 1, only one bump B is shown as being enlarged, actually large number of bump B are disposed on the substrate K, as shown in FIG. 3. Then, the diameter of the bump B is around one hundred and several ten $\mu m$, if many bumps B of 1000 are provided in the area of 10 mm×10 mm on the substrate K in the configuration shown in FIG. 3, the position of the many bumps B, which is captured by a CCD camera as the imaging device 3, slightly come off from the imaging central axis M.

As shown in FIG. 5, a length L to the lens provided in the CCD camera as the imaging device 3 is long of 300 mm. And, even though the height is also same on either bump B in the imaging range (the imaging area), as the bump B is nearer to the imaging central axis M, the value measured (detected) as a distance between the first measuring point and the second measuring point becomes a closer value of the XS in proportion to an actual height H. And in the imaging area of capturing an image at one time, in a bump B away from the imaging central axis M, the detected value (the distance between the measuring points) includes some error $\Delta x$.

In FIG. 6, it is possible that image data captured from an imaging central axis M1 which leans toward the light emission apparatus 2 side shows a distance between the first measuring point and the second measuring point as XS+$\Delta x$. Reversibly, it is possible that image data captured from an imaging central axis M2 which leans toward opposite side of the light emission apparatus 2 side shows a distance XB between the first measuring point and the second measuring point with XS−$\Delta x$. Aforesaid $\Delta x$ shows an error.

Superscription $\Delta x$ can be easily calculated on all bumps in the imaging area. However, in this embodiment, if the detection error is in the range of a value that is beforehand measured in proportion to the height H of the bump that is allowed, the error $\Delta x$ is made to be an allowable error. Although similar error also exists in a relationship between the light emission apparatus 2 and the bump position, the description thereof is omitted.

Therefore, in this embodiment, on each bump B in the imaging area obtained by capturing an image at one time, it is judged that it is a bump with a height H which is similar to the standard bump BS, if it is within an allowed range of the detection error, i.e., the distance XB between the measuring points is in a range of XS−$\Delta x \leq$ XB $\leq$ XS+$\Delta x$.

Figure 4:
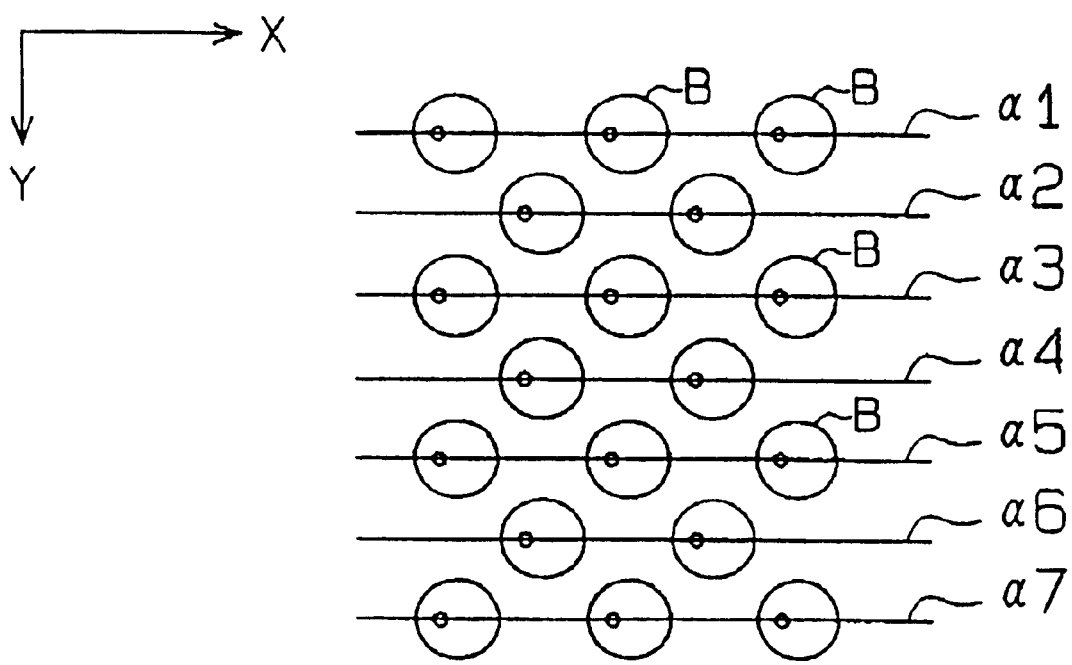
FIG. 4 is a main section plan of the FIG. 3.

When the distance XB between the measuring points satisfies the reference value in step 40, it is determined whether a counter C for the number of the bumps has reached the predetermined number n in step 50. Namely, it is determined whether the determination with respect to the distance XB between measuring points has been carried out with respect to all bumps B in image data. When a decision with respect to the distance XB between measuring points has not been finished with respect to all bump B in the image data, the routine returns to step 20, and steps 20–40 are carried out with respect to the bump which adjoins along the X direction. And, when the processing along the inspection line α in the X direction is complete, the inspection line α is moved in a Y direction by a predetermined inspection interval, and steps 20–40 are carried out with respect to the bump B along a new inspection line α. In FIG. 4, the inspection lines α are illustrated as α1–α7. In this embodiment, the inspection is carried out in order from the α1 with the inspection interval shown in FIG. 4.

In aforesaid step 50, when the decision processing are carried out with respect to all bump B in the image data read in step 10, a measurement completion processing is carried out at step 60, and this routine is once finished.

And in aforesaid step 40, when the distance XB between the measuring points does not satisfy the reference value, it is judged that an inferior bump exists, and the routine goes to step 70 in order to outputting an inferior signal (a NG signal) showing an existence of the inferior bump, and this processing routine is finished.

Therefore, when this apparatus is connected with a control equipment of a removal robot which is provided in a product line of a factory, a substrate K with the inferior bump is excluded from the product line based on the inferior signal by the aforesaid removal robot in the subsequent process. Or, when an alarm device such as a warning lamp or a warning buzzer is operated based on the inferior signal, a worker removes the substrate K from the line based on the operation of the alarm device.

Aforesaid step 20 corresponds to an operation means, and step 40 corresponds to a judgment means.

(Second Embodiment)

Second embodiment, which materialized the third invention, is explained with reference to FIGS. 8–11. Different compositions are mainly explained, while same characters indicate the same compositions in the first embodiment.

Figure 8:
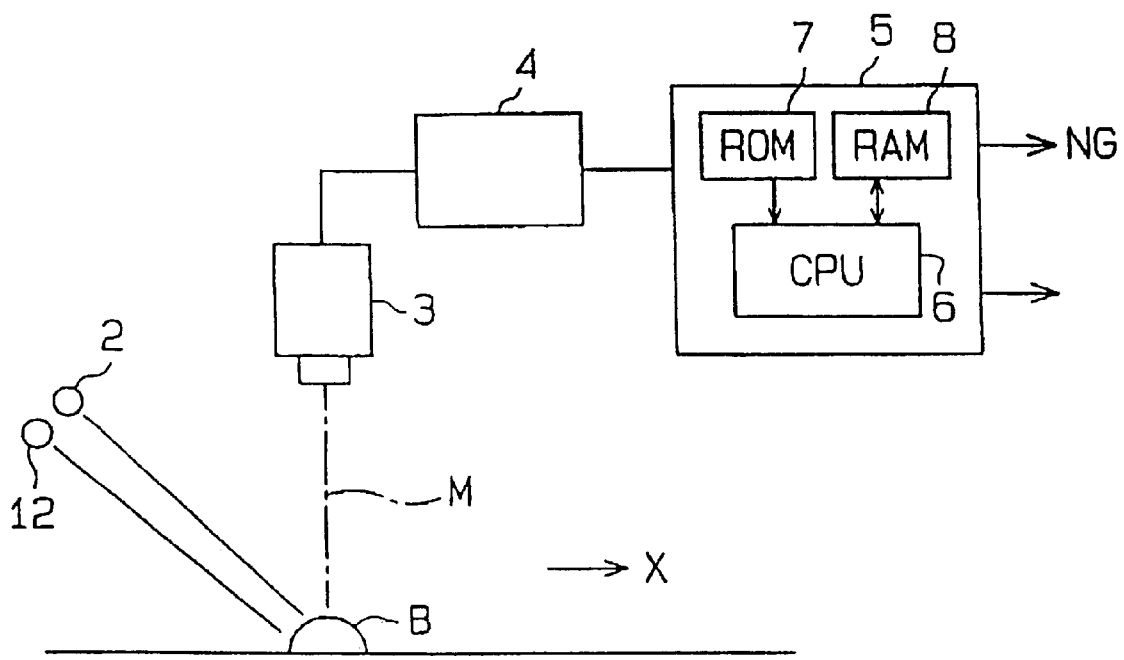
FIG. 8 is a schematic drawing of an apparatus for judging whether a bump height is proper or not according to an embodiment of the second invention.
Figure 11:
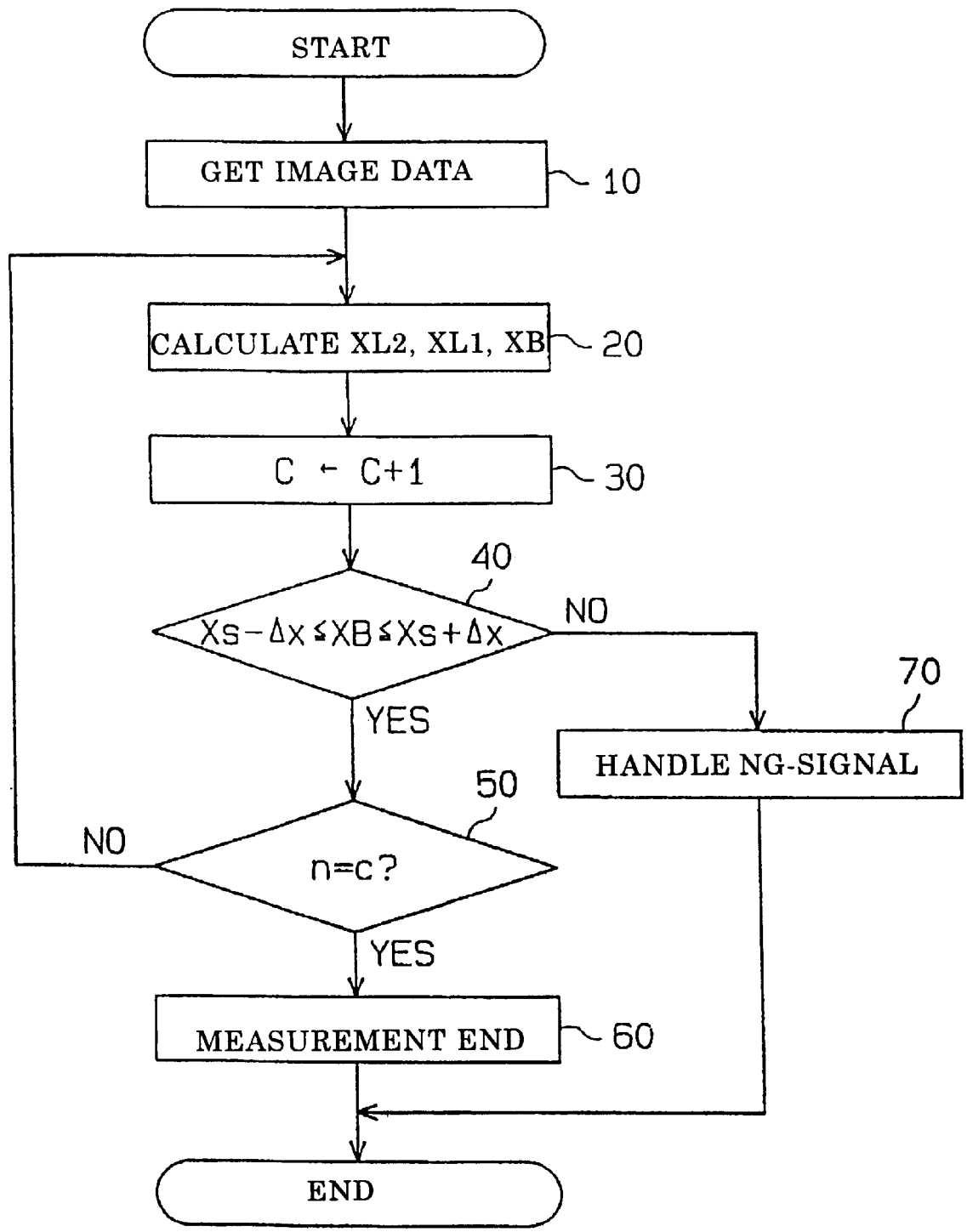
FIG. 11 is a flowchart of judging of the apparatus for judging whether a bump height is proper or not in the same embodiment.

In this embodiment, a light emission apparatus 12 is provided in addition to a light emission apparatus 2, as shown in FIG. 8. Both light emission apparatuses 2,12 are disposed obliquely above a bump B so that both light emission apparatuses 2,12 may be located in a radial direction of the bump viewing the bump B from above. It is desirable that both light emission apparatuses 2,12 are disposed separately to be a parallel light source to the bump. Then, as shown in FIG. 11, in this embodiment, step 20A is carried out instead of carrying out step in the bump height decision processing routine in the first embodiment, and further step 40A is carried out instead of carrying out step 40.

Figure 9:
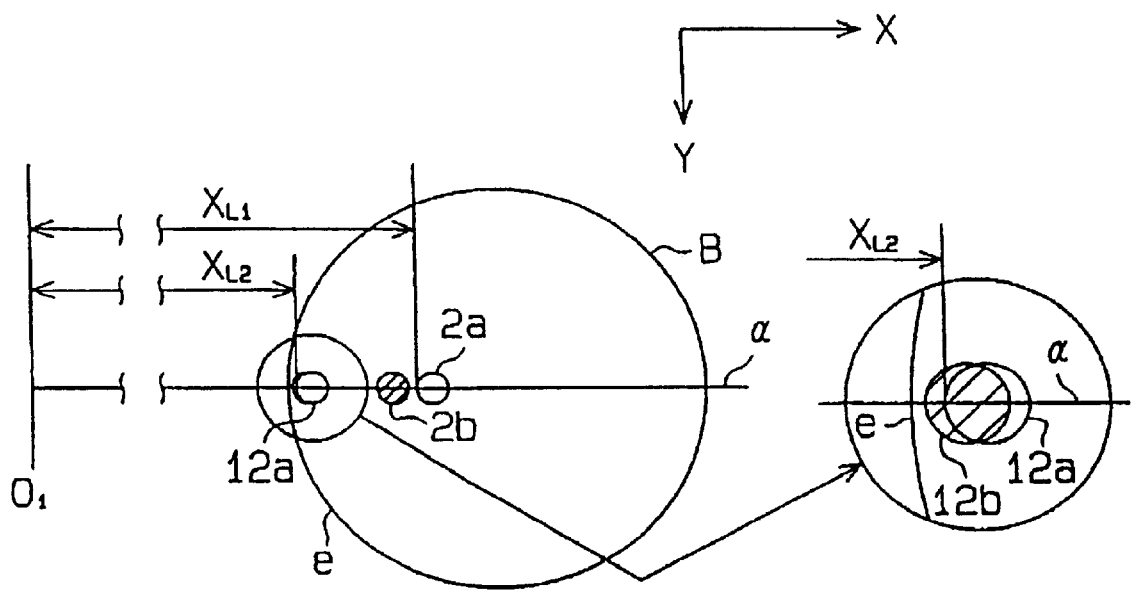
FIG. 9 is a plan of a bump including an image of a light source, which is reflected in the bump surface in the same embodiment.

At step 20A, as shown in FIG. 9, an edge of a reflection region 12a of the light emission apparatus 12 and a reflection region 2a of the light emission apparatus 2 are detected along an inspection line α, and XL1 and XL2 and XB are calculated.

These measurement calculations are carried out as follows. To begin with, along the inspection line α on the diameter of the bump B, a distance XL2 between an origin O1 (a starting point of the inspection line of image datum) and an edge of a reflection region 12a of the light emission apparatus 12 on the bump B is calculated. And distance XL1 between the origin O1 and an edge of a reflection region 2a of the light the emission apparatus 2 on the bump B is calculated. Then, the difference XB between the XL1 and the XL2 is calculated.

In this embodiment, the edge of the reflection region 12a of the light emission apparatus 12 on the bump B corresponds to a second measuring point, and the edge of the reflection region 2a of the light emission apparatus 2 on the bump B corresponds to a first measuring point, and the XB corresponds to a distance between measuring points.

Figure 10:
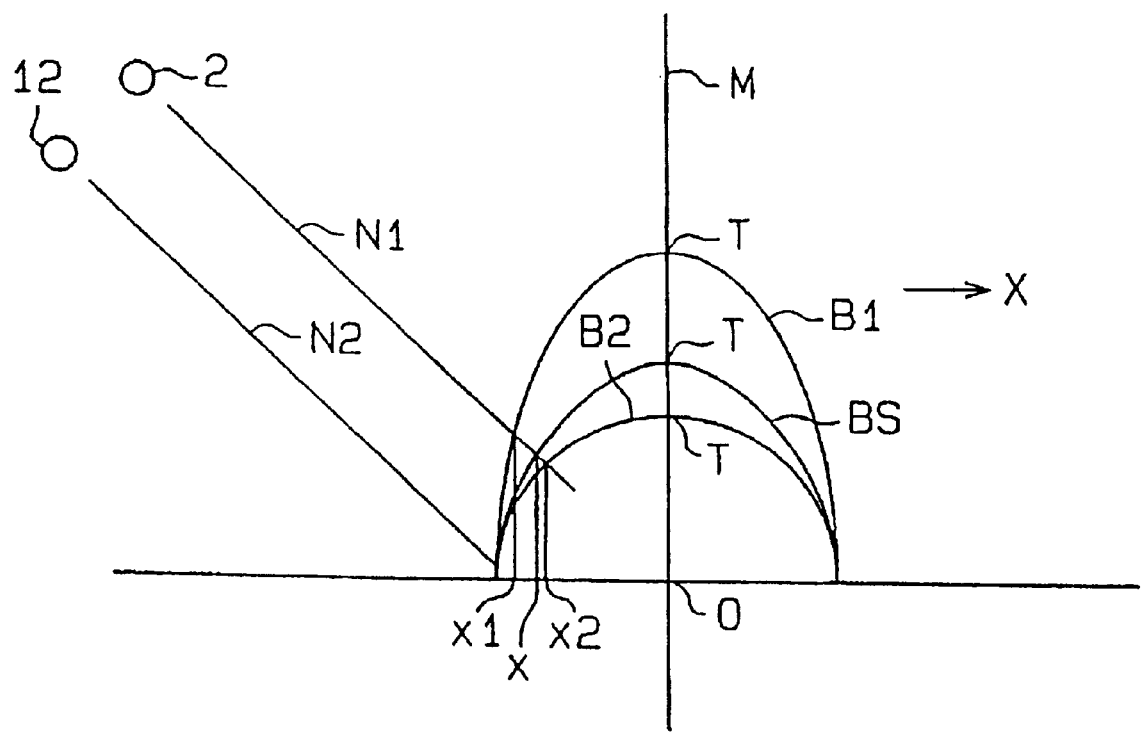
FIG. 10 is an explanatory drawing of a situation in which the image of the light source is reflected on the bump of which the height differs in the same embodiment.

As shown in FIG. 10, when a bump B2 is lower than a standard bump BS, an edge of a reflection region 2a of the light emission apparatus 2 within the picture data is a position x2 which is shifted to a top T (a center point O) of the bump B. Reversibly, when a bump B1 is higher than the standard bump BS, an edge of a reflection region 2b within the picture data is in a position x1, which is shifted to a bump edge e.

In the meantime, when the bump B2 is lower than the standard bump BS, the edge of the reflection region 12a of the light emission apparatus 12 on the bump within image data is in a position which is shifted to the bump edge e. However, a distance Δx1 between the aforesaid position which is shifted to the bump edge e and the position in the standard bump BS becomes (x2−x)>>Δx1, since the CCD camera as an imaging device 3 works in a perpendicular optical system.

And, when the bump B1 is higher than the standard bump BS, the edge of the reflection region 12a of the light emission apparatus 12 within image data is in a position which is shifted to the center O of the bump. However, a distance Δx2 between the aforesaid position which is shifted to the bump center O and the position in the standard bump BS becomes (x2−x)>>Δx2, since the CCD camera as the imaging device 3 works in the perpendicular optical system.

For example, in FIG. 9, the reflection region 2b of the light emission apparatus 2, which is shown as an area with hatching, is shifted to the bump edge e side rather than to the reflection region 2a. In the meantime, the reflection region 12b of the light emission apparatus 12, which is shown as an area with hatching, is shifted to the bump edge e side rather than to the reflection region 12a. As shown in this figure, a migration length of the reflection region 2a of the light emission apparatus 2 is far bigger than a migration length of the reflection region 12b of the light emission apparatus 12.

In this embodiment, a reference value is set considering the above-mentioned point. As well as aforesaid embodiment, the reference value is calculated by adding a detection error Δx to a distance XS between an edge (a second measuring point) of the reflection region 12a of the light emission apparatus 12 and an edge (a first measuring point) of the reflection region 2a of the light emission apparatus 2. A reason why the detection error occurs is a same reason in the first embodiment.

Therefore, similarly in this embodiment, with respect to each bump B in the imaging area obtained by one time picturization, it is judged that it is a bump with a height H which is similar to the standard bump BS, if it is within an allowed range of the detection error, i.e., the distance XB between measuring points is in a range of XS−Δx≦XB≦XS+Δx.

(Third Embodiment)

Figure 12:
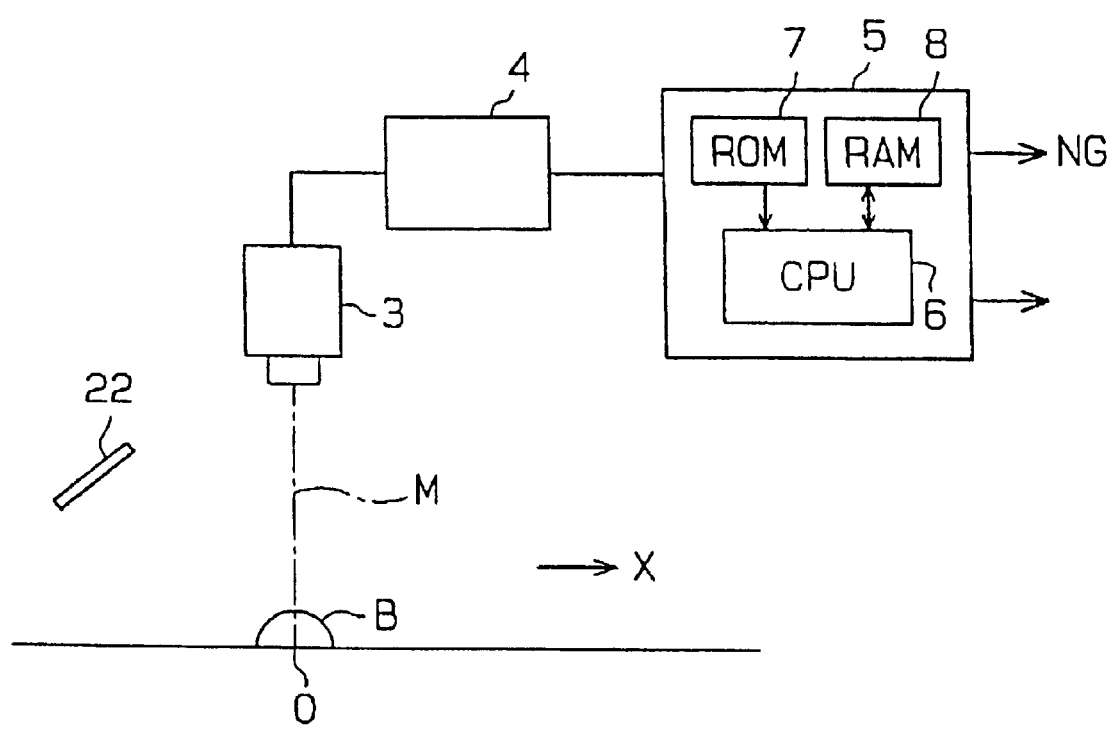
FIG. 12 is a schematic drawing of an apparatus for judging whether a bump height is proper or not according to an embodiment of the third invention.

Third embodiment, which materialized third invention, is explained with reference to FIGS. 12–14. In this embodiment, as shown in FIG. 12, a pair of the point light sources (the light emission apparatuses 2,12) in the second embodiment is substituted with one line light source (a light emission apparatus 22). The light emission apparatus 22 is disposed so that, when picturized by the imaging device 3, in image data, a length direction of a reflection region 22a of the light emission apparatus 22 may be along the radial direction of the bump B.

In this embodiment, at step 20A of the bump height decision processing routine in the second embodiment, the first measuring point is detected as an edge, which is shifted to a top T (a center point O) of a reflection region 22a of the light emission apparatus 22. Similarly, the second measuring point is detected as an edge, which is shifted to a bump edge e of the light emission apparatus 22, and a distance XB between both these measuring points is calculated.

Figure 13:
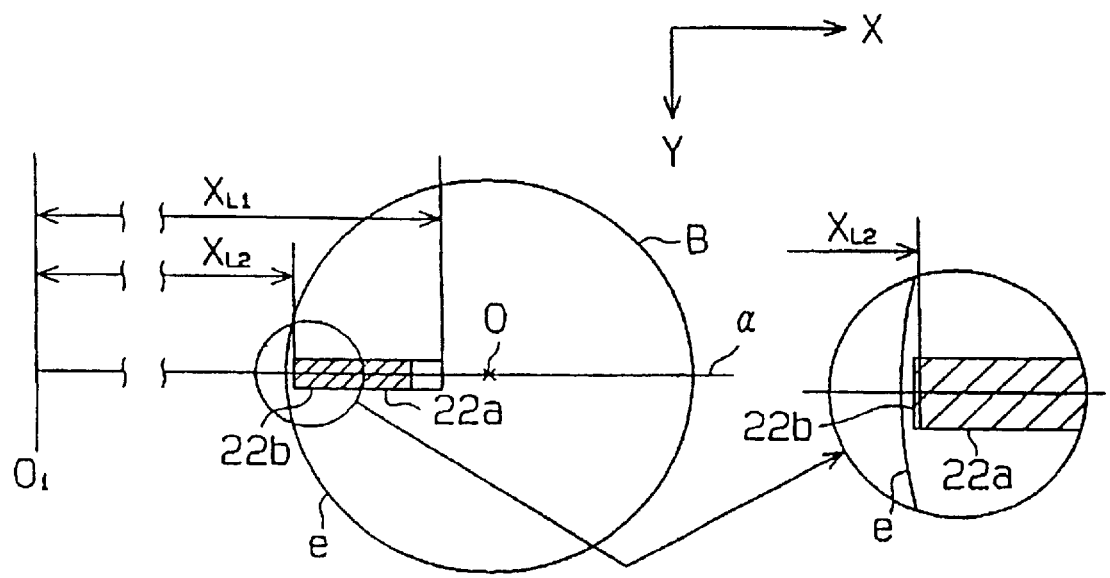
FIG. 13 is a plan of the bump including an image of a light source, which is reflected in the bump surface in the same embodiment.
Figure 14:
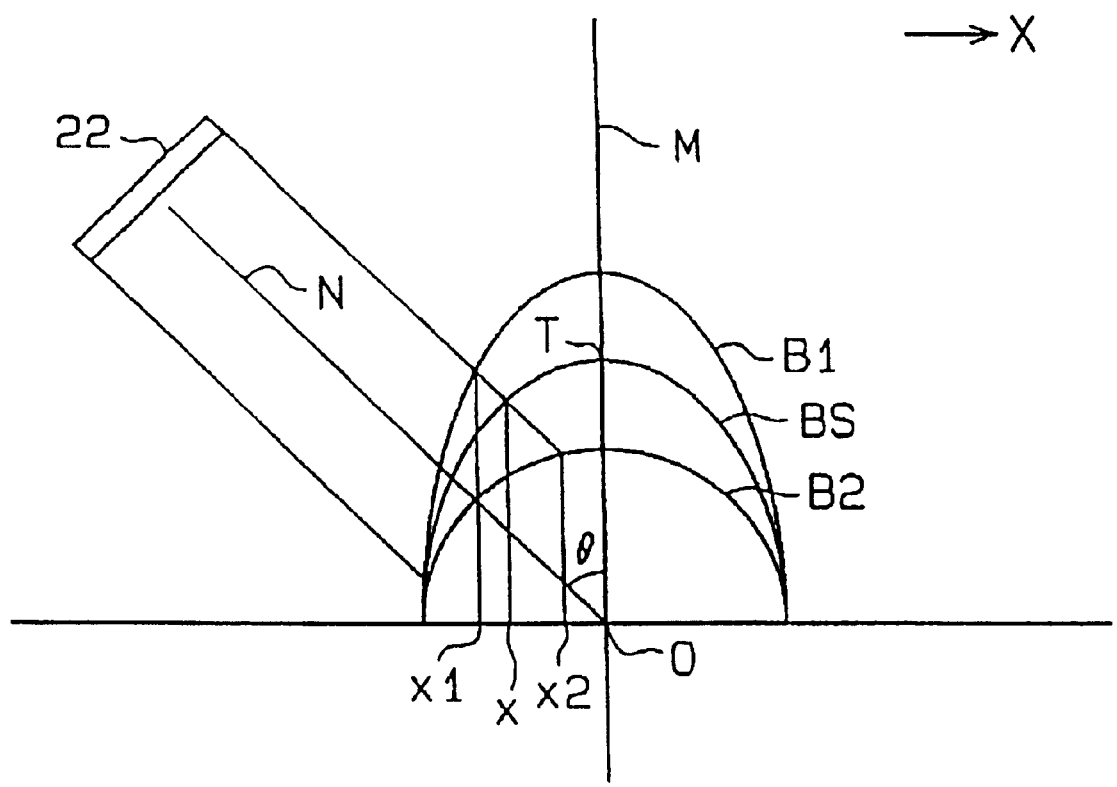
FIG. 14 is an explnatory drawing of a situation in which the image of the light source is reflected on the bump of which the height differs in the same embodiment.

That is to say, as it shown in FIGS. 13 and 14, along an inspection line α on a diameter of the bump B, a distance XL2 between an origin O1 (a starting point of the inspection line within image data) and an edge which is shifted to the bump edge e of the light emission apparatus 22 is calculated, and a distance XL1 between the origin O1 and an edge which is shifted to the top T (the center point O) of the reflection region 22a of the light emission apparatus 2 on the bump B is calculated. Then, the difference XB between the XL1 and the XL2 is calculated.

Still, in this embodiment, an detection error Δx is added to the distance XS by the reason which is explained in the first embodiment and second embodiment. Therefore, a function and an effect are similar to those of the second embodiment.

Still, an embodiment of the present invention is not limited to embodiments described above, and it is apparent that numerous improvements and modifications can be made thereto within the scope not departing from the concept of the invention. For example, the present invention can be made as following.

(1) Although the CCD is an area sensor in the aforesaid embodiments, it may be a line sensor. In this case, it may be picturized by moving the CCD or the substrate in X direction or Y direction. In the case, the mobile speed may be set in proportion to the resolution of the CCD.

(2) In each embodiment, although the area sensor type CCD camera is adopted as an imaging device, the galvanic type may be adopted.

(3) Though in each embodiment, the light emission apparatus 2,12,22 is adopted, there is no necessity that the object, which emits light. For example, objects such as white and silver color whose brightness is high may be reflected in the bump surface. Or, the light may be indirectly reflected on the surface of the bump with the reflection of the light applied to the object.

(4) In each embodiment, although the ROM and the RAM are adopted as the memory means, only the ROM or only the RAM can constitute the memory means.

INDUSTRIAL APPLICABILITY

As explained above, the present invention can provide an apparatus for judging a bump height, capable of efficiently and moreover reliably judging whether a bump height is proper or not.

What is claimed is:

1. An apparatus to check a height of a bump, comprising:
    an imaging device configured to be provided above the bump and configured to capture a surface image of a surface of the bump;
    a reference object provided such that an image of the reference object reflected in the surface of the bump is viewed from the imaging device;
    a measuring device configured to measure, based on the surface image captured by the imaging device, a distance between an image position in the image of the reference object reflected in the surface of the bump and a predetermined position which is positioned on a line connecting the image position and a center of the bump such that the image position exists between the center and the predetermined position; and
    a determining device configured to determine whether the height of the bump is within a predetermined range by comparing the distance with a reference distance.

2. An apparatus according to claim 1, wherein the predetermined position is positioned at an edge of the bump.

3. An apparatus according to claim 1, further comprising:
    an additional reference object provided such that an additional surface image of the additional reference object reflected in the surface of the bump is viewed from the imaging device, the predetermined position being a position in the additional image.

4. An apparatus according to claim 1, wherein the reference object is a point-source light.

5. An apparatus according to claim 1, wherein the reference object is a line source which is provided such that a longitudinal direction of the image of the reference object reflected in the surface of the bump is substantially parallel to the line, and wherein the image position is one end of the image of the reference object on a side of the center along the line and the predetermined position is another end of the image of the reference object on a side of an edge of the bump along the line.

6. An apparatus according to claim 1, wherein the reference object does not emit light and has a high brightness.

7. An apparatus according to claim 6, wherein a color of the reference object is white or silver.

8. An apparatus according to claim 1, wherein the predetermined range is determined based on an error which is caused by that the imaging device is not positioned right above the bump.

9. An apparatus to check a height of a bump, comprising:
    imaging means for capturing a surface image of a surface of the bump, the imaging means being provided above the bump;
    a reference object provided such that an image of the reference object reflected in the surface of the bump is viewed from the imaging means;
    measuring means for measuring, based on the surface image captured by the imaging means, a distance between an image position in the image of the reference object reflected in the surface of the bump and a predetermined position which is positioned on a line connecting the image position and a center of the bump such that the image position exists between the center and the predetermined position; and
    determining means for determining whether the height of the bump is within a predetermined range by comparing the distance with a reference distance.

* * * * *